United States Patent [19]
Glenn et al.

[11] Patent Number: 6,132,358
[45] Date of Patent: Oct. 17, 2000

[54] SHIELD ASSEMBLY FOR RADIOACTIVE STENTS

[75] Inventors: Richard A. Glenn; Thomas H. Campbell, both of Redwood City, Calif.

[73] Assignee: IsoStent, Inc., Belmont, Calif.

[21] Appl. No.: 09/236,770

[22] Filed: Jan. 25, 1999

[51] Int. Cl.$^7$ .................................................. A61N 5/00
[52] U.S. Cl. ................................................. 600/3; 600/7
[58] Field of Search ..................... 600/1–8; 250/515.1, 250/505.1, 506.1; 252/478

[56] References Cited

U.S. PATENT DOCUMENTS

| | | | |
|---|---|---|---|
| 5,460,592 | 10/1995 | Langton | 600/7 |
| 5,605,530 | 2/1997 | Fischell et al. | |
| 5,814,824 | 9/1998 | Mussman | 250/515.1 |

OTHER PUBLICATIONS

U.S. application No. 8/990,381, Fischell et al., filed Dec. 1997.

*Primary Examiner*—Cary O'Connor
*Assistant Examiner*—Catherine McPherson
*Attorney, Agent, or Firm*—Beyer Weaver & Thomas, LLP

[57] ABSTRACT

A radiation shield assembly (30) for a radioactive stent (11) which includes a first shield member (31) having a first mating surface (32) and a second shield member (33) having an opposed second mating surface (35). When the two shield members are removably coupled to one another, the first mating surface (32) cooperates with the opposing second mating surface (35) to substantially radially enclose the stent (11) therebetween, and substantially prevent the direct passage of radioisotopes emitted from the stent radially out of the shield assembly (30).

31 Claims, 6 Drawing Sheets

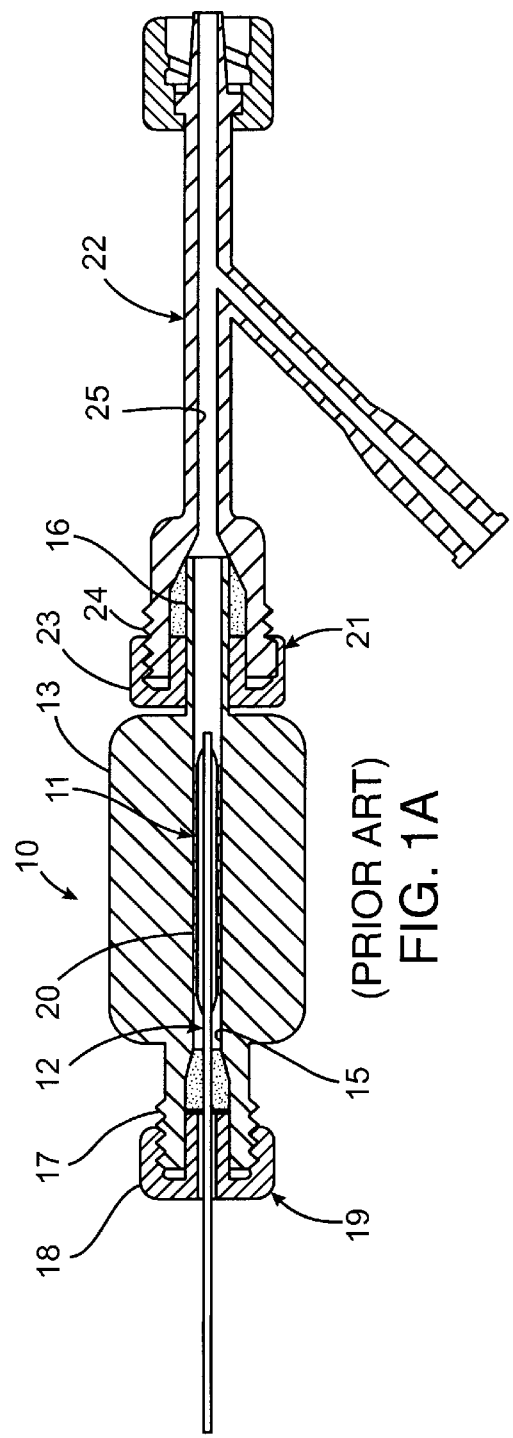
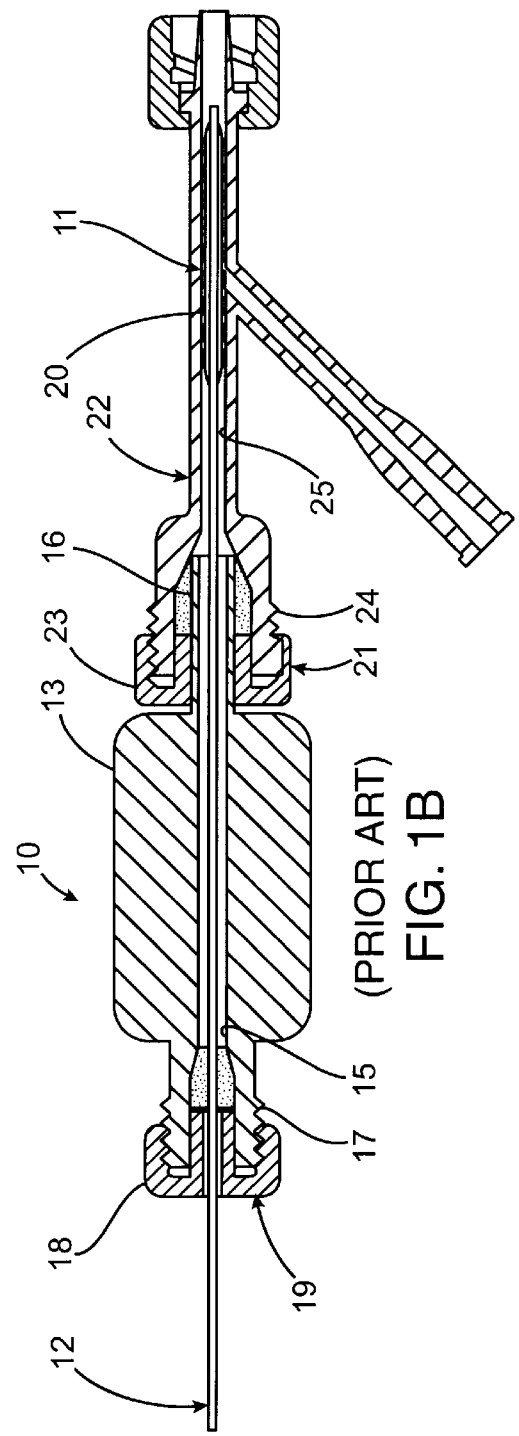
FIG. 1A (PRIOR ART)
FIG. 1B (PRIOR ART)

SHIELD ASSEMBLY FOR RADIOACTIVE STENTS

TECHNICAL FIELD

The present invention relates, generally, to shield assemblies for radioactive devices and, more particularly, to radiation shields for radioactive stents and delivery catheters.

BACKGROUND OF THE INVENTION

Percutaneous Transluminal Angioplasty (PTA) is a medical procedure for widening a stenosis or constriction of a bodily passage. The most common application is to widen the passage of a blood vessel, such as an artery, which has been constricted by the build-up of cholesterol fats or atherosclerotic plaque. When this medical procedure is applied to a coronary artery, it is referred to as Percutaneous Transluminal Coronary Angioplasty (PTCA).

Typically, a tip mounted balloon of a balloon catheter is advanced over a guidewire to the stenosis. Once the balloon catheter is properly positioned, the balloon is inflated to compress the plaque against the vessel walls and widen the stenosis. Problems occur, however, when the dilatation of the occlusion forms fissures, flaps and/or dissections which may ultimately cause reclosure or restenosis of the vessel.

To maintain vessel patency and/or strengthen the area undergoing angioplasty or other treatment, an intravascular prosthesis may be employed. These devices are usually introduced percutaneously, transported transluminally and positioned at a desired location within the widened stenosis of the patient. One form of an intravascular prosthesis is a radially expandable stent device which is typically positioned at the tip of a balloon delivery catheter in a crimped condition. When the tip of the delivery catheter apparatus and the crimped stent are properly positioned at the desired location or the stenosis, the balloon is expanded to implant the stent in the widened vessel. In some instances, expansion of the balloon portion of the delivery catheter can simultaneously compress the plaque at that location and expand the stent to its proper implantation size. The balloon portion of the catheter is then deflated and withdrawn from the vessel, leaving the implanted radioactive stent as a permanent scaffold and as a deterrent to tissue growth in order to reduce the chance of restenosis.

More recently, these stents have been embedded or implanted with radioisotopes so that they emit predictable amounts of radiation into the widened vessel and immediate surrounding area. The nature of these radioactive devices is that regrowth of the tissue can be reduced by the radiation, an effect which is highly beneficial in preventing restenosis of the vessel.

Although these radioactive stents only emit relatively low levels of radiation, direct contact with the stent by physicians, laboratory technicians, and other personnel should be avoided. As a result, shielding devices 10 such as those shown in FIGS. 1A and 1B have been developed to enable the safe transportation and handling of radioactive stent 11 and/or a stent delivery catheter apparatus 12. Typical of these shield devices 10 is disclosed in U.S. Pat. No. 5,605,530 entitled "System for Safe Implantation of Radioisotope Stents" which is incorporated by reference in its entirety.

These radioactive shield devices 10 typically include one piece main body portions 13 having longitudinally extending central lumens 15 therethrough. Positioned in these lumens 15 in a retracted condition (FIG. 1A) are the stent delivery catheter apparatus 12 and crimped radioactive stent 11 for shielding thereof. Accordingly, this one-piece configuration enables safe transportation and handling of the radioactive stent before being inserted into the vessel.

The radiation shield device 10 further preferably includes a distal proboscis 16 and a proximal threaded section 17 which operates as a Tuohy-Borst fitting 19 onto which a nut 18 can be screwed. When the expandable balloon 20 of the delivery catheter and the distal mounted radioactive stent 11 are retracted in the central lumen 15 of the shield device 10 (FIG. 1A), a shield nut 18 may be tightened down on proximal threaded section 17, thereby frictionally coupling the stent delivery catheter apparatus 12 therein.

To insert the stent delivery catheter apparatus 12 and stent 11 into a vessel (not shown), the proboscis 16 of the shield device 10 is preferably inserted into another Tuohy-Borst fitting 21 of a guiding catheter. This union may be provided by a Y-adapter 22 having an adapter nut 23 tightened to the threaded end 24 to functionally couple and fluid seal the radiation shield device to the Y-adapter. Subsequently, the proximal shield nut 18 may be loosened to enable the mounted stent 11 and the delivery catheter apparatus 12 to be forwardly advanced (FIG. 1B) into a passage 25 of the Y-adapter 22 and into the vessel as a unit.

While this one-piece shield device is most adequate to shield personnel from radiation exposure from the radioactive stent, several problems are inherent in the design. For example, when the radiation shield device 10 is mounted to the Y-adapter 22, and the delivery catheter is slideably inserted through the central lumen of the shield device and the passage 25 of the Y-adapter, the radiation shield device cannot be removed or separated from the delivery catheter apparatus 12 since the diameter of the central lumen is not sufficiently large to enable the proximal manipulating end of the catheter apparatus (not shown) to slide therethrough. Consequently, the depth of insertion of the delivery catheter is limited to the proximal end of the radiation shield device (i.e., the Tuohy-Borst fitting 19) rather than the proximal end of the Y-adapter 22 (i.e., the Tuohy-Borst fitting 21). Therefore, the useable length of the catheter 12 is decreased. Increasing the length of the catheter apparatus to compensate for the decrease of insertion depth may be problematic since any increase in length may incrementally reduce the ability to precisely control the stent placement. This configuration also limits the physicians choice of delivery catheters to only those provided with the stent.

Moreover, even should a length increase be unnecessary, manipulation of the catheter apparatus is still more difficult since the surgeon must now control the catheter from relatively cumbersome shield device as compared to the smaller proximal end of the Y-adapter. This is especially true in instances where the shield device 10 has been decoupled from the Y-adapter during stent deployment. The mere weight and bulkiness of the shield device 10 dangling from the catheter apparatus significantly reduces maneuverability and manipulation of the catheter. In fact, in some instances, care must be observed so that the weight of the shield device 10 does not retract the stent assembly from the vessel.

Another problem associated with this arrangement is that after the stent delivery catheter apparatus 12 and the mounted radioactive stent 11 have been passed through the central lumen 15 of the shield device 10 into the passage of the Y-adapter, it is difficult to reinsert the catheter apparatus and the stent back into the central lumen of the shield device 10, should this be necessary to abort the deployment procedure. Therefore, there is a need to enable removal of the radiation shield device from the delivery catheter apparatus during deployment of the stent.

SUMMARY OF THE INVENTION

To achieve the foregoing, the present invention relates to a two piece shield assembly which is capable of being removed from the stent delivery catheter while the delivery catheter apparatus is inserted into a vessel for deployment of the stent. The radiation shield assembly includes a first shield member having a first mating surface and a second shield member having an opposed second mating surface. The two shield members are removably coupled to one another, the first mating surface cooperating with the opposing second mating surface to substantially radially enclose the stent therebetween, thereby substantially preventing the direct passage of radioisotopes emitted from the stent radially out of the shield assembly.

In one embodiment, the first mating surface of the first shield member and the second mating surface of the second shield member cooperate to define a longitudinally extending channel therebetween. This channel is formed and dimensioned for longitudinal receipt of the stent therein. Preferably, the first mating surface defines a first channel portion, and the second mating surface defines a second channel portion. Collectively, the first channel portion and the second channel portion cooperate to define the channel when the first and second shield members are mounted together to enclose the stent therein.

To align the first and second shield members, another configuration is provided wherein the first mating surface of the first shield member defines a first alignment prong on one side of the channel. The second mating surface of the second shield member further defines a first recess formed and dimensioned for receipt of the first alignment prong therein to align the first and second channel portions when the first and second shield members are mounted together to enclose the stent in the channel. The first alignment prong preferably extends substantially longitudinally along the channel from the one end of the shield assembly to the opposite end thereof, while the first recess extends substantially longitudinally along the channel from the one end of the shield assembly to the opposite end thereof.

In another embodiment, the radiation shield assembly includes a coupling device movably coupling the second shield member to the first shield member between a closed position and an open position. In the closed position, the two shield members and the coupling device cooperate to enclosing at least a stent delivery catheter apparatus in the channel, while in the open position, the stent delivery catheter may be removed from the shield assembly. This coupling device is preferably provided by a hinge member movably mounting one edge of the first mating surface of the shield member to an opposed edge of the second mating surface of the second shield member between the first and open positions.

In accordance with an alternative aspect of the invention, each of the two shield members includes a support wall intersecting the channel and two alignment walls, one on each side of the channel disposed at an angle skewed relative to the support wall. The shield members are mounted together to enclose the stent and catheter apparatus in the channel with each respective alignment wall of the shield member engaging the corresponding respective opposed alignment wall on the other shield member. In a preferred embodiment, the shield members can be coupled together by a pin member removably positioned in and extending through both shield members.

BRIEF DESCRIPTION OF THE DRAWINGS

The method and assembly of the present invention has other objects and features of advantage which will be more readily apparent from the following description of the Detailed Description of the Embodiments and the appended claims, when taken in conjunction with the accompanying drawing, in which:

FIGS. 1A and 1B are a sequence of cross-sectional side elevation views of a prior art one-piece radiation shield assembly coupled to a Y-adapter, and illustrating sliding movement of an enclosed delivery catheter and mounted radioactive stent from the shield assembly to the Y adapter.

DETAILED DESCRIPTION OF THE EMBODIMENTS

Figure 2A:
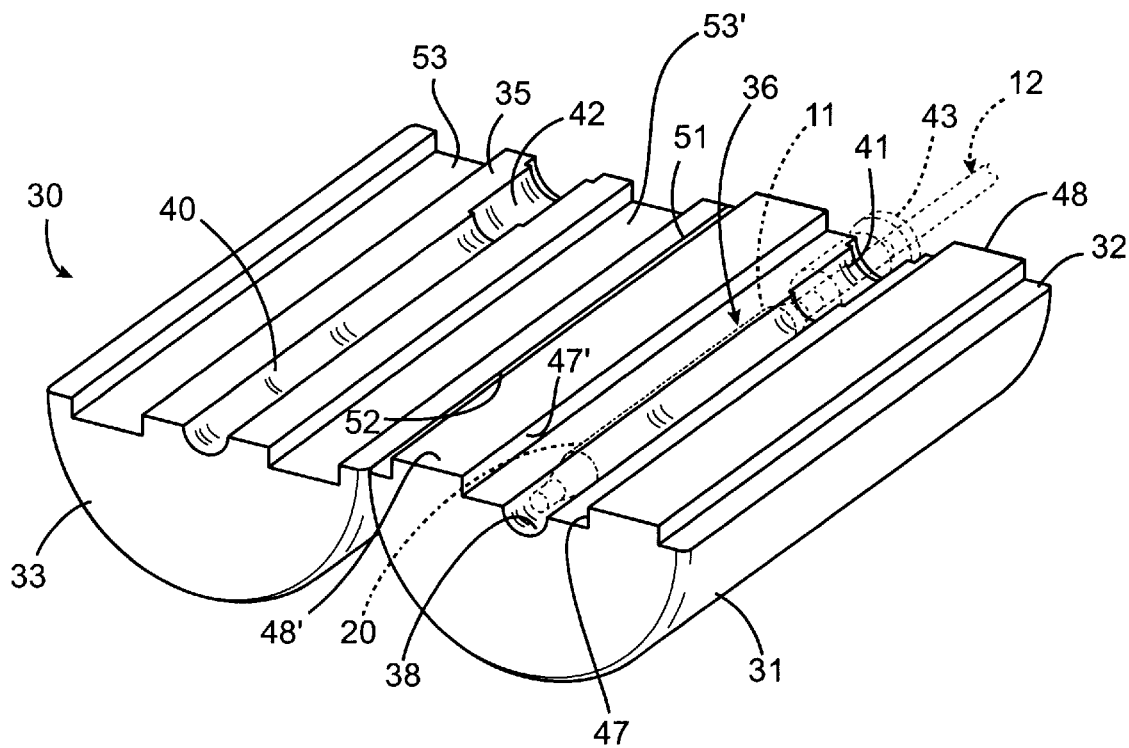
FIGS. 2A and 2B are a sequence of top perspective views of a first embodiment of a two piece radiation shield assembly constructed in accordance with the present invention, and illustrating movement between a closed position, enclosing at least the radioactive stent in a channel, and an open position, enabling removal of the radioactive stent the shield assembly.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Figure 2B:
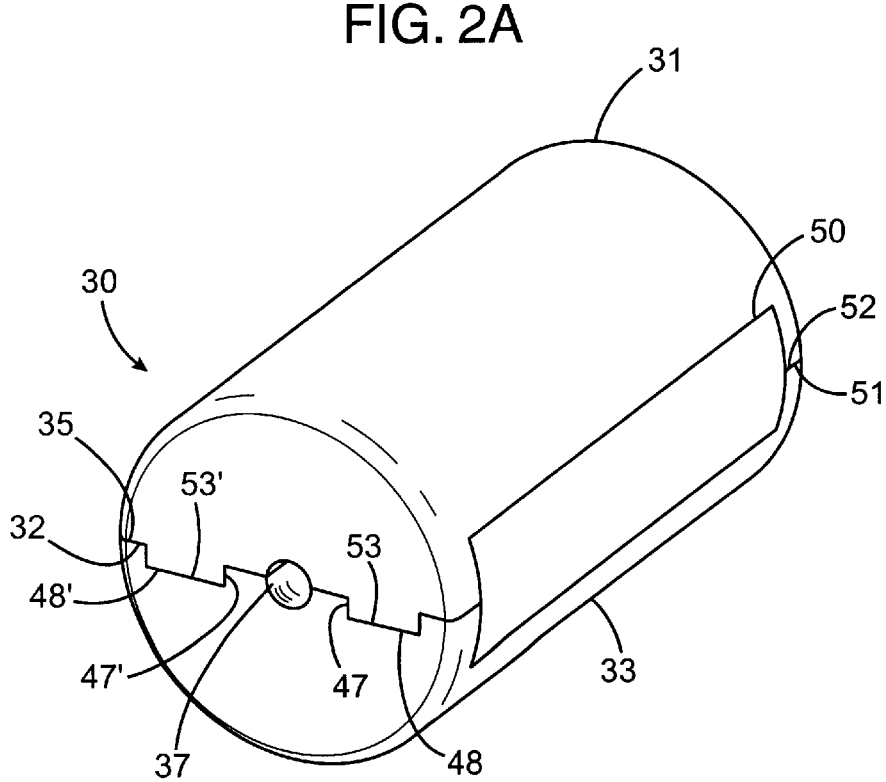

Referring now to FIGS. 2A and 2B, a radiation shield assembly, generally designated 30, is illustrated for shielding a radioactive stent 11 which is mounted to a distal portion of a stent delivery catheter apparatus 12 (both shown in dotted lines in FIG. 2A). The radiation shield assembly 30 includes a first shield member 31 having a first mating surface 32 and a second shield member 33 having an opposed second mating surface 35. The two shield members are removably coupled to one another, and the first mating surface 32 of the first shield member 31 and the second mating surface 35 of the second shield member 33 cooperate to substantially radially enclose the stent 11 therebetween in a manner substantially preventing the direct passage of radioisotopes emitted from the stent radially out of the shield assembly 30.

Accordingly, a two-piece radiation shield assembly 30 is provided which, in the "closed" position of FIG. 2B, functions to enclose both the distal portion of the stent delivery catheter apparatus and the mounted radioactive stent therein (hereinafter, the "stent assembly 36"). Thus, the radioactive stent maybe handled, transported and deployed without directly exposing personnel to the radiation emitted by the stent. However, the two shield members 31, 33 may be selectively oriented in an "open" position (FIG. 2A) which enables the shield assembly to be removed from the stent delivery catheter apparatus while the radioactive stent and distal portion of the catheter apparatus are being transvascularly maneuvered to the stenosis. Thus, the useable maneuvering length of the catheter apparatus is increased which increases depth insertion. Additionally, the ease of manipulating the position of the mounted stent 11 and expandable balloon 20 of the catheter apparatus 12 itself is augmented since the bulky radiation shield assembly will no longer impede movement. Moreover, in instances where the deployment procedure of the stent must be aborted, the stent assembly may be easily reinserted or retracted back into the shield assembly by fully or partially opening the two-piece shield.

Although the present invention is described herein in connection with radioactive stents and stent delivery catheters, it should be well understood to those skilled in the art that the present invention is not limited to these applications. For example, the shielding assembly of the present invention may be implemented in situations that require shielding of radioactive stents delivered from means other than stent delivery catheters, the delivery of other radioactive devices such as radioactive grafts, radioactive wires, radioactive coils, and radioactive balloon catheters or any combination thereof.

In the preferred embodiment, each shield member 31, 33 is semi-cylindrical in shape so that in the closed position a cylinder is formed. It will be appreciated, however, that other shapes are permissible as long as the structure provides adequate radiation shielding from the radioactive stent enclosed therein. To position the stent assembly 36 in the shield assembly 30, a channel 37 extends from one end of each shield member to an opposite end thereof which is formed and dimensioned for sliding receipt of the stent assembly therein. Moreover, to provide proper shielding from the radioisotopes emitted from the radioactive stent 11, the shield assembly in a closed position (FIG. 2A) must be of sufficient radial dimension or diameter to prevent passage of the particle therethrough. Thus, the necessary thickness of the shield assembly is a function of the shield material and the type of radioisotope emitted from stent. For example, when the shield members are formed from a moldable acrylic and the stent is embedded with a low energy (less than about 5.0 MeV) beta particle emitter such as Phosphorus 32 ($^{32}P$), or a beta and gamma emitter such as Iridium 192 ($^{192}Ir$), the diameter of the shield assembly should be between about 1.0 inch to about 2.0 inches, and most preferably about 1.0 inches. Other suitable materials, of course, may be employed in whole or in part, such as a polycarbonate, acrylic/polycarbonate with a thin leaded outer shell or a high density metallic material or the like.

As best viewed in FIG. 2A, the length of each shield member 31, 33 is preferably slightly longer than the length of the distal portion of the catheter expandable balloon 20 and the mounted stent 1. This assures adequate shielding from the radioisotopes which are emitted from the radioactive stent 11 generally in directions radially from a longitudinal axis of the stent. Preferably, the length of the shield members extend about 1.0 cm to 2.0 cm past the proximal and distal ends of the stent.

In accordance with the present invention and as indicated above, the first shield member 31 includes a first mating surface 32, while the second shield member includes a second mating surface 35. When the shield assembly 30 is positioned in the closed position (FIG. 2B), the first and second mating surface 32, 35 are opposed one another, and are further configured to mate in a manner substantially radially enclose the stent 11 therebetween. Preferably, as shown in the first embodiment of FIGS. 2A and 2B, the first mating surface 32 of the first shield member 31 defines a longitudinally extending first channel portion 38, while the second mating surface 35 thereof forms a second channel portion 40. These channel portions are preferably semi-cylindrical in shape and are positioned substantially co-axial with the shield assembly longitudinal axis. In the closed position, these channel portions cooperate to form channel 37 which is dimensioned for sliding and axial receipt of the stent assembly 36 therein.

At the proximal end of each channel portion 38, 40 is a semi-cylindrical bore portion 41, 42 having a diameter larger than that of the respective channel portion 38, 40. When oriented in the closed position, these bore portions 41, 42 collectively define a bore which is configured for receipt of an O-ring seal or first Tuohy-Borst fitting 43 (shown in broken lines) or the like therein. Thus, the stent assembly 36 may be releasably locked into the retracted position inside the shield assembly 30 upon tightening of the fitting 43.

Figure 3:
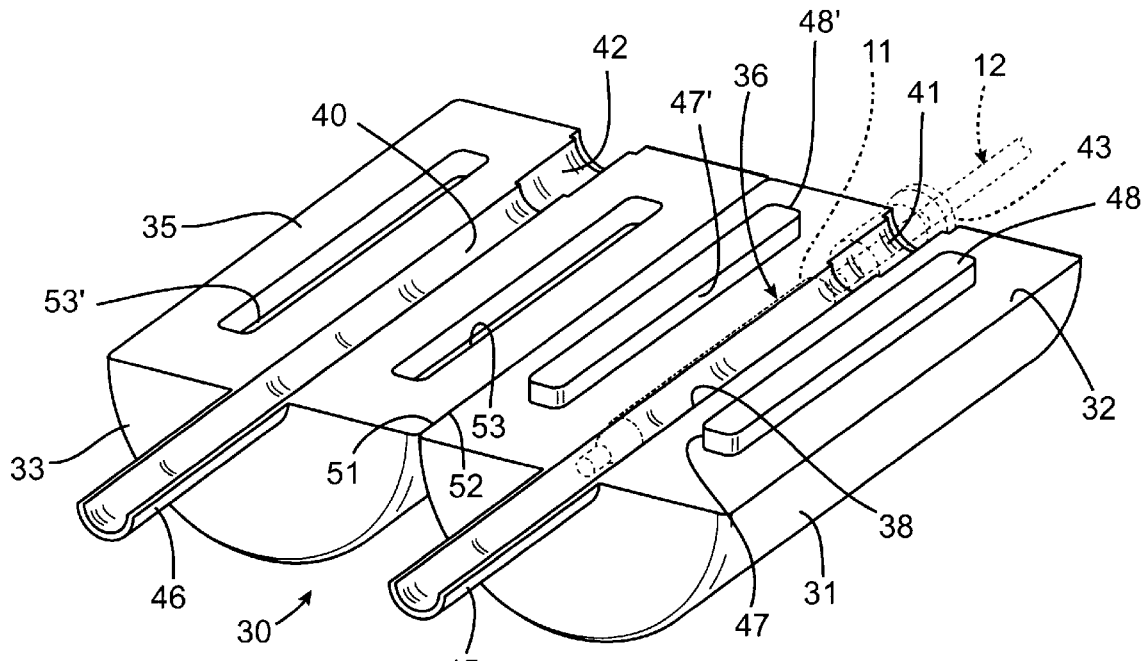
FIG. 3 is a top perspective view of a second embodiment of the present invention two piece radiation shield assembly in the open position.

On the opposite distal end of the first and second shield members 31, 33 may be a first proboscis portion 45 and a second proboscis portion 46 (FIG. 3), respectively, which extend distally therefrom. In the closed position (not shown), these proboscis portions 45, 46 collectively form a proboscis which is preferably dimensioned thereof for receipt in a second Tuohy-Borst fitting or the like (not shown). Similar to the prior art embodiment of FIGS. 1A and 1B, the first and second Tuohy-Borst fittings may be adjusted so that the stent assembly 36 may be advanced through a Y adapter and into a vessel for deployment of the stent. It will further be appreciated that while only the embodiment of FIG. 3 illustrates the addition of a proboscis, any of the embodiments of the present invention may also include one.

In accordance with the present invention, the first and second mating surface 32, 35 cooperate to substantially prevent the passage of radioisotopes between the opposed shield member 31, 33, when in the closed position. As the radioisotopes are emitted from the stent, they travel along relatively linear paths, and away from the stent outer surface in directions generally radially away from the longitudinal axis of the stent. Thus, some of these radioisotopes will initially pass through the gap formed between the first mating surface 32 of the first shield member 31 and the second mating surface 35 of the second shield member 33 both of which internally terminate at the channel 37. On an atomic level this gap formed between the first mating surface 32 and the second mating surface 35 may be relatively large in some regions. Accordingly, the first and second mating surfaces are configured to eliminate any direct linear paths which extend from the channel 37 to an exterior portion of the shield assembly 30.

Figure 4:
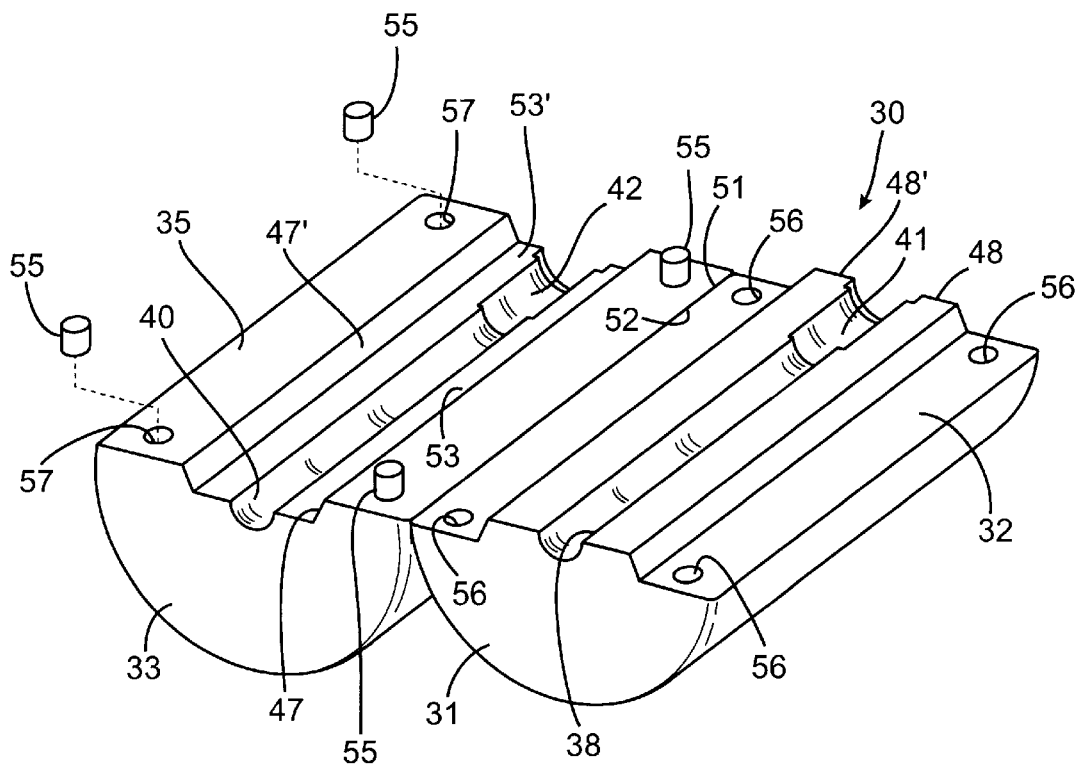
FIG. 4 is a top perspective view of a two piece radiation shield in the open position in accordance with a third embodiment of the invention.
Figure 7:
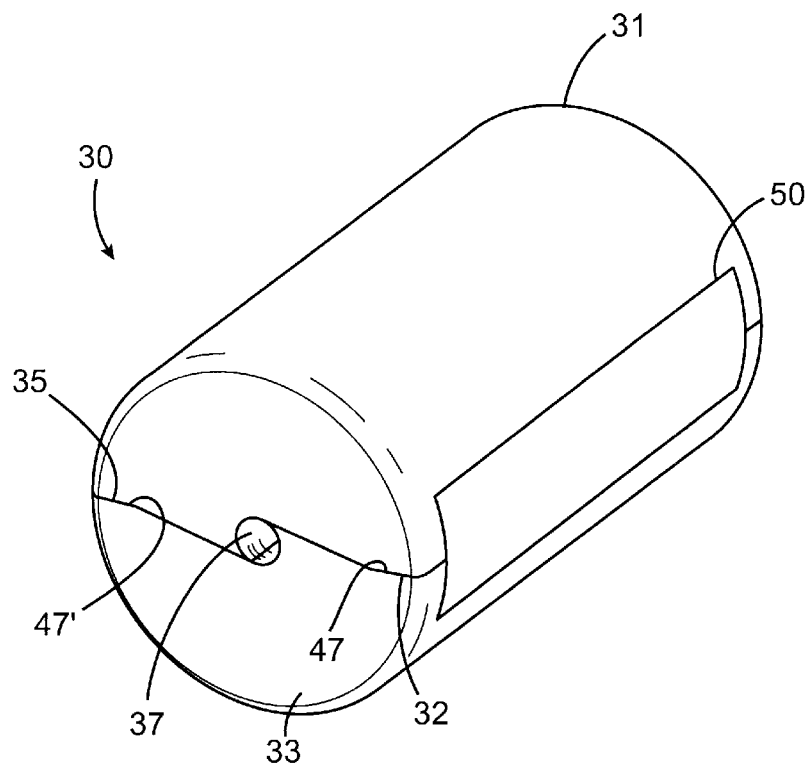
FIG. 7 is a top perspective view of a two piece radiation shield in the closed position in accordance with a sixth embodiment of the invention.
Figure 8:
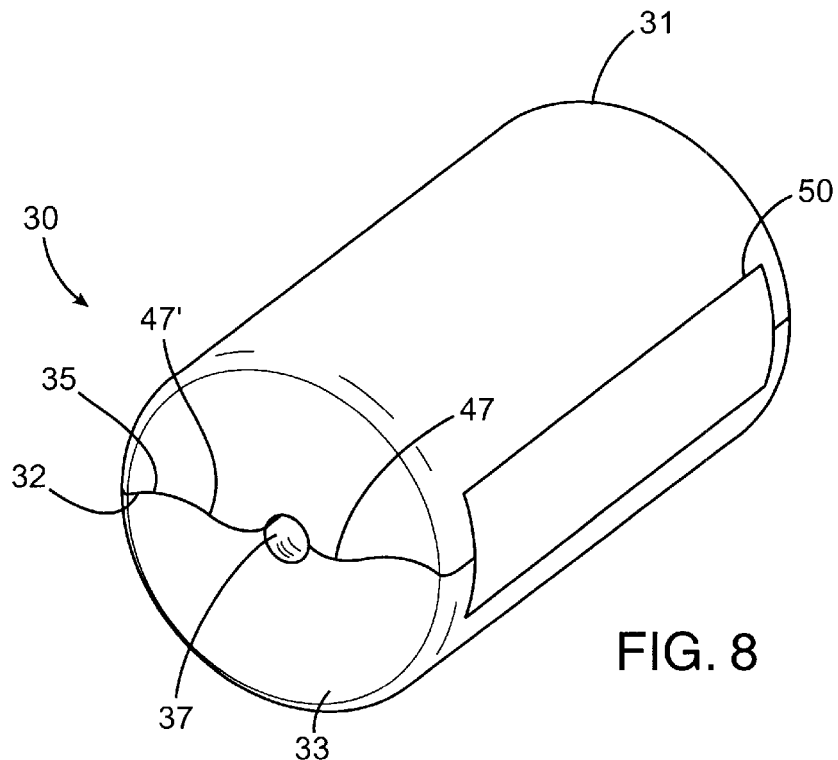
FIG. 8 is a top perspective view of a two piece radiation shield in the closed position in accordance with a seventh embodiment of the invention.

Referring back to FIGS. 2A and 2B, for example, the opposed first and second mating surface 32, 35 may be substantially planar for the most part to ease manufacture. However, at some position therealong, the respective surface 32, 35 will be sufficiently skewed relative these planes containing the surfaces such that radioisotopes emitted from the stent which are travelling between and in a direction relatively parallel to these opposed planes will contact this skewed surface. Therefore, at least one of the first mating surface 32 and the second mating surface 35 includes a side wall portion 47, 47' which is sufficiently skewed relative the plane to prevent passage of these linearly traveling radioisotopes through surface gap and out of the shield assembly 30. These side wall portions 47, 47' need not be perpendicular to the respective plane, but may be tapered, as shown in the embodiment of FIG. 4, or may be relatively gradually sloped, as viewed in the embodiment of FIG. 7. Moreover, the side wall portions 47, 47' may even be curvilinear (FIG. 8), as long as an isotope passing linearly between the opposed first and second mating surfaces would eventually impact one of these side wall portions thereof. Essentially, in any linear direction, an isotope will be physically stopped by a consistent solid material having a sufficient thickness specific to the isotope (E.g., about 0.29 in. acrylic for Phosphorus 32 ($^{32}$P)).

In the preferred embodiment, each side wall portion 47, 47' extends substantially longitudinally along the respective shield member 31, 33 from a proximal end to a distal end thereof. Further, these walls extend substantially parallel to the longitudinal axis of the channel 37, although it will be understood that they may be relatively skewed as well. As viewed in the embodiment of FIG. 3, the side wall portions 47, 47' may only extend partially along the respective channel portions 38, 40. In this arrangement, the length of the side wall portions 47, 47' are preferably at least substantially equal to the length of the radioactive stent 11 mounted to the delivery catheter apparatus 12. Moreover, to assure containment of the radioisotopes, the side portions preferably extend longitudinally along the channel at positions substantially adjacent the stent 11 when in the stent assembly 36 is in the retracted position. FIG. 3 best illustrates this concept by providing first and second alignment prongs 48, 48' (to be discussed below in greater detail) at an orientation adjacent to the stent 11. These prongs include side wall portions sufficiently long and properly oriented to substantially prevent the radioisotopes from passing through the gap and out of the shield assembly.

A coupling device, generally designated 50, preferably couples the second shield member 33 to the first shield member 31 for movement between the opened position (FIG. 2A) and the closed position (FIG. 2B). In one embodiment, the coupling device may be provided by a hinge member 50 or the like movably mounting one edge 51 of the first mating surface 32 to an opposed edge 52 of the second mating surface. Thus, the first shield member 31 is pivotally mounted to the second shield member between the opened and closed position, and about a longitudinal axis positioned at the opposed edges 51, 52 of the shield members. For example, the hinge member may be a mechanical door-type hinge or simply a strip of adhesive tape 50. As another example, the coupling device may be provided by a perforated shrink wrap material shrunk around the two halves retaining them in an aligned form. When removal of the shield assembly from the catheter is necessary, the shrink wrap may be torn or removed from the shield assembly so that the shield members may be separated.

On the opposite side of each shield member 31, 33, mating latch members (not shown) may be provided which releasably latch the shield members together in the closed position. Upon unlocking of the latch members, the shield assembly may be pivotally moved to the opened position so that the stent assembly or catheter assembly can be removed. These latch members may be provided by any conventional latch devices employed in the field.

To facilitate alignment between the first shield member 31 and the second shield member so that the respective channel portions 38, 40 align for receipt of the stent assembly 36 in the closed position, the shield assembly 30 preferably includes an alignment device therebetween. In one embodiment, the alignment device may be provided by a longitudinally extending first alignment prong 48 (FIGS. 2, 3 and 5) upstanding from the first mating surface, and positioned on one side of the first channel portion 38. This first alignment prong 48 preferably extends from proximate one end of the first channel portion 38 to proximate an opposite end thereof, and is preferably oriented substantially parallel to the channel portion.

More preferably, the prong extends completely from the proximal end of the shield assembly to the distal end thereof.

The second mating surface 35 of the second shield member 33 provides a first recess 53 formed and dimensioned for sliding receipt of the first alignment prong 48 therein. Such receipt is preferably relatively tight so as to properly align the first and second channel portions 38, 40 when the first and second shield members are mounted together in the closed position. However, the tolerance must not be so small as to substantially impede or prevent movement of the shield assembly 30 between the closed position and the opened position.

In a similar manner, on the opposite side of the respective channel portions 38, 40, the first mating surface 32 and the second mating surface 35 preferably define a second alignment prong 48' and a corresponding second recess 53'. In the closed position, the first and second alignment prongs 48, 48' are slideably received in the respective first and second recesses 53, 53' for alignment of the first shield member 31 with the second shield member 33. Similar to the first alignment prong the second alignment prong 48' upstands from the first mating surface 32 of the first shield member 31, and preferably longitudinally extends from the proximal end of the shield assembly to the distal end thereof. As shown in the embodiment of FIG. 3, however, the alignment prongs 48, 48' and corresponding recesses 53, 53' may only extend from proximate one end of the respective channel portion 38, 40 to an opposite end thereof.

The side walls defining the height of the first and second prongs 48, 48' may upstand substantially perpendicular from the first mating surface 32, as shown in FIGS. 2A and 2B. Alternatively, in the embodiment of FIG. 3, these side walls may be tapered inwardly to facilitate opening and closing of the shield assembly. In this configuration, the opposed side walls defining the corresponding recesses 53, 53' would be similarly tapered for mating therebetween. Moreover, it will be appreciated that these prongs and corresponding recesses may be interchanged on the mating surfaces without departing from the true spirit and nature of the present invention.

Turning now to FIGS. 4 and 5, the present invention may include dowel pins 55 or the like as an alignment device. Thus, to properly align the first and second shield members 31, 33 in the closed position, at least two dowel pins 55 are employed on opposite sides of the channel portions 38, 40. Preferably, however, four dowel pins 55 are strategically positioned at or proximate to the four corners of the first and second mating surface 32, 35. Corresponding dowel bores 56 and 57 are formed into the mating surface 32, 35 and are configured for sliding receipt of a respective dowel pin 55 therein. Therefore, the dowel bores 56 of the first mating surface 32 must be co-axially aligned with the dowel bores 57 of the second mating surface 35 for align receipt of the dowel pin.

The dowel pins may be more permanently anchored to one of the first shield member 31 or the second shield member 33, or a combination thereof. This assures that the dowel pin will not inadvertently dislodge from the corresponding dowel bores 56, 57 during separation from of the shield members the closed position to the opened position. Moreover, these dowel pins 55 may be adapted to provide a snap-type fit with the corresponding dowel bore for additional securing purposes. In this arrangement, these alignment dowel pins may further function as the coupling device and/or as a latch device between the two shield members. This may be especially true of the configuration of FIG. 4 where alignment prongs 48, 48' are already provided.

In accordance with the present invention, the alignment prongs 48, 48' and corresponding recesses 53, 53' may also integrally provide the side wall portions 47, 47' extending longitudinally along the channel 37. Thus, either the side walls of the prongs 48, 48' or the side walls of the recesses 53, 53' form the side wall portions 47, 47 necessary to impede passage of the radioisotopes out of the shield assembly. Accordingly, the alignment prongs 48, 48', such as those shown in FIG. 3, must be sufficiently thick to shield radiation exposure. As mentioned above, this calculation is in part dependent upon the prong composition and the intensity of the radioisotope embedded in the stent 11.

Figure 5A:
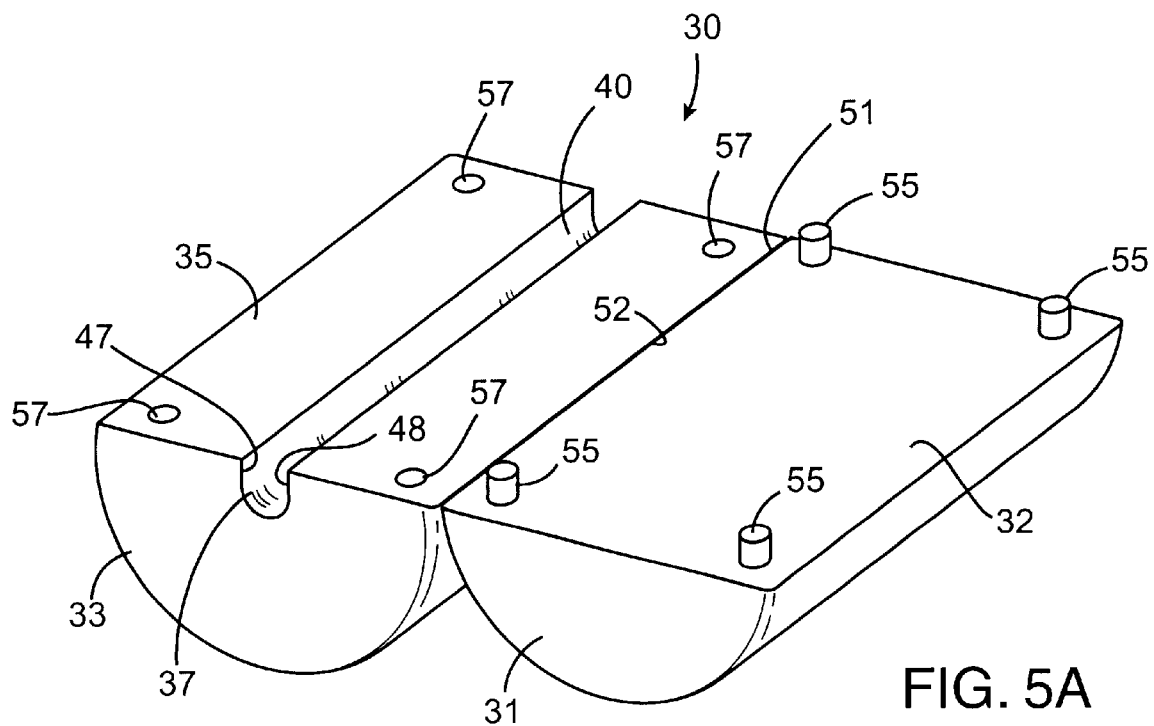
FIGS. 5A and 5B are a sequence of top perspective views of a fourth embodiment of the present invention illustrating movement between the closed position and the open position.

Referring now to FIGS. 5A, an alternative embodiment of the present invention is provided wherein the first mating surface 32 of the first shield member 31 is substantially planar, while the second mating surface 35 of the second shield member 33 primarily defines the channel 37. In this embodiment, the stent assembly (not shown) is located in the U-shaped second channel portion 40 at a position sufficiently below the gap formed between the first mating surface 32 and the second mating surface 35 in the closed position. The radioisotopes emitted substantially linearly from the stent surface, accordingly, cannot not enter the gap in a direction substantially parallel thereto. This embodiment, thus, substantially contains the radioisotopes within the shield assembly 30 since these particles entering the gap will eventually impact the first mating surface 32 of the first shield member 31.

Figure 5B:
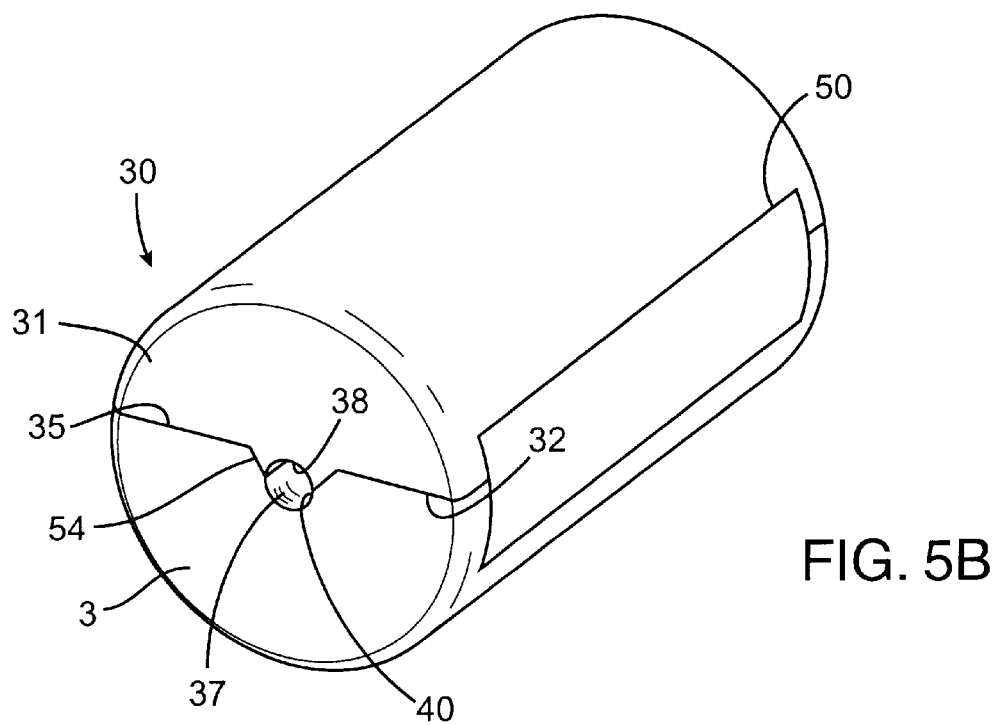

Similarly, in the embodiment of FIG. 5B, a pair of off-set first and second shield members 31, 33 are provided having substantially planar respective first and second mating surfaces 32, 35. In this embodiment, however, the first mating surface 32 provides a longitudinally extending protrusion portion 54 forming a semi-cylindrical first channel portion 38. This protrusion portion 54 has tapered outer walls formed to extend into the opposed U-shaped second channel portion 40 in an aligned manner such that in the closed position, the protrusion portion 54 cooperates with the U-shaped channel portion 40 to enclose a stent therein. Unlike the previous embodiment, a substantially cylindrical channel 37 is formed.

Figure 6A:
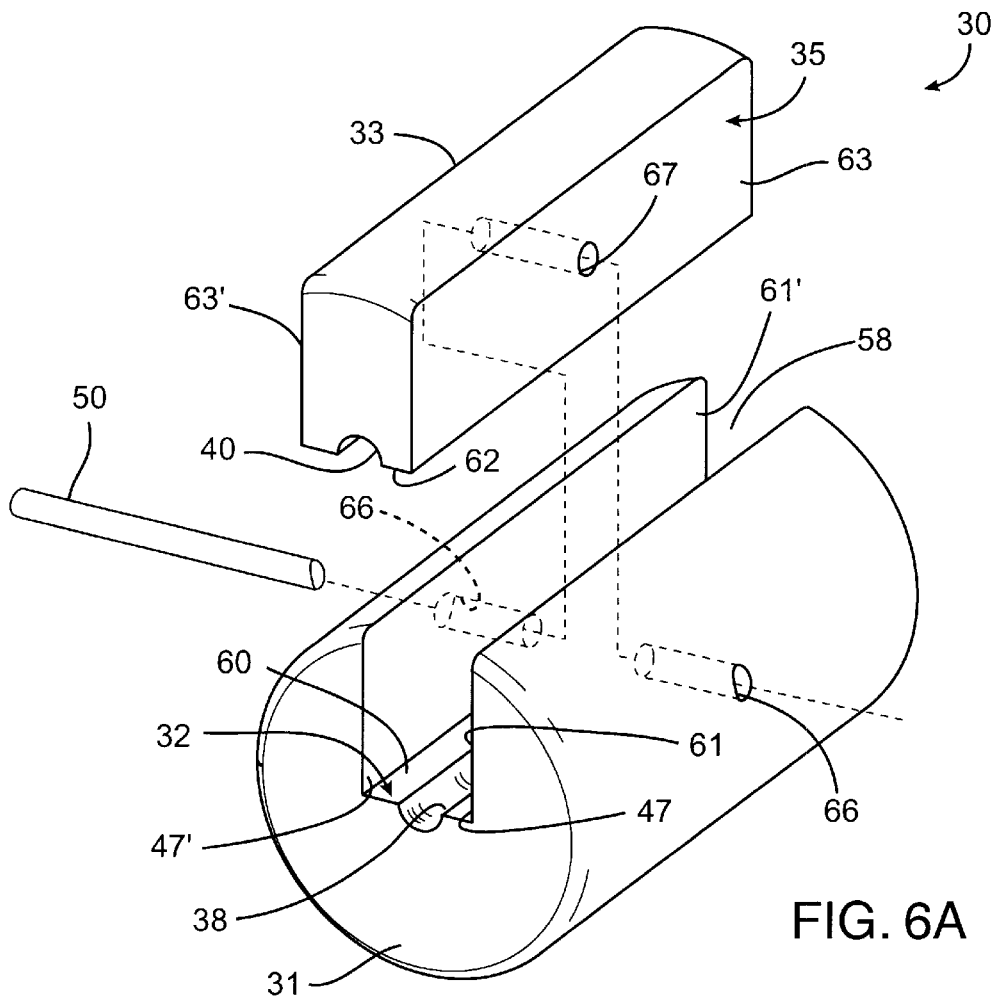
FIGS. 6A and 6B are a sequence of top perspective views of a fifth embodiment of the present invention illustrating movement between the closed position and the open position.
Figure 6B:
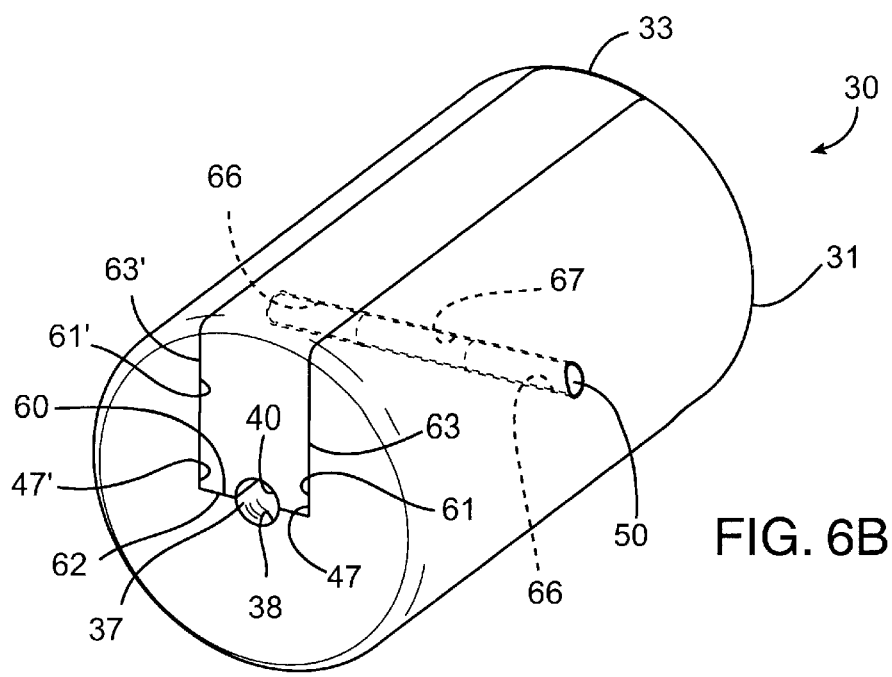

In the embodiment of FIGS. 6A and 6B, a radiation shield assembly 30 is provided wherein the first mating surface 32 of the first shield member 31 defines a longitudinally extending receiving slot 58 formed and dimensioned for sliding receipt of a key-shaped second shield member 33 between the open position (FIG. 6A) and the closed position (FIG. 6B). According to the present invention, the first mating surface 32 of the first shield member 31 and the second mating surface 35 of the second shield member 33 cooperate to substantially radially enclose the stent 11 therebetween in a manner substantially preventing the direct passage of radioisotopes emitted from the stent radially out of the shield assembly 30.

The first mating surface 32 further includes a first support wall 60 defining the first channel portion 38. On each side of the first support wall 60 is a first alignment wall 61 and an opposite second alignment wall 61', each of which is disposed at an angle skewed relative to the first support wall 60. As shown in FIGS. 6A and 6B, the first and second alignment walls 61, 61' are preferably substantially perpendicular to first support wall 60. However, this skewed angle may be oblique or obtuse as well. Collectively, the first support wall 60, the first alignment wall 61 and the second alignment wall form the receiving slot 58.

The second mating surface of the second shield member 33 provides a second support wall 62 defining a second channel portion 40. Hence, in the closed position (FIG. 6B), the first and second channel portions 38, 40 cooperate to define the channel 37 formed for receipt of the stent assembly 36. It will be understood, however, that the configuration of FIGS. 5A and 5B may be employed as well.

Similar to the first shield member 31, on each side of the second support wall 62 is a first contact wall 63 and an opposite second contact wall 63', each of which is disposed at an angle skewed relative to the second support wall 62. The skewed angle of the contact walls 63, 63' relative the second support wall 62, of course, must be substantially equal to that between the opposed alignment walls 61, 61' and the first support wall 60. Accordingly, the second shield member 33 is formed and dimensioned for sliding receipt in the receiving slot 58 of the first shield member 31 between the opened and closed position. Moreover, the spacing 20 of the As shown in FIGS. 6A and 6B, the first and second alignment walls 61, 61' are preferably substantially perpendicular to first support wall 60. However, this skewed angle may be oblique or obtuse as well.

The first support wall 60, and the first and second alignment walls 61, 61' of the first shield member 31 all extend longitudinally from the proximal end of shield assembly 30 to the opposite distal end thereof, while the second support wall 62, and the first and second contact walls 63, 63' of the second shield member 33 all extend longitudinally from the proximal end to the opposite distal end of the shield assembly. As illustrated in FIG. 6B, when the first alignment wall 61 and the second alignment wall 61 respectively engage the first contact wall 63 and the second contact wall 63', and the first support wall 60 engages the second support wall 62, the first shield member 31 slidably couples together with the second shield member 33 toward the closed position. When properly aligned, the first channel portion 38 and the second channel portion 40 cooperate to form channel 37 which slideably receives stent assembly (not shown) therein. As previously indicated, this cooperation between the first mating surface and the second mating surface substantially prevents the direct passage of radioisotopes emitted from the stent radially out of radiation shield assembly 30.

While this embodiment illustrates the skewed walls at about 90°, it will be understood that any other angles may be employed which are sufficient to prevent the passage of the linearly directed isotopes emitted from the channel 37.

A coupling device 50 is provided to couple the second shield member 33 to the first shield member when oriented in the closed position. As best viewed in FIG. 6A, the coupling device is preferably provided by a pin member 50 that is removably positioned in and extending through first shield member 31 and second shield member 33 when the two are mounted together in a closed position. To position the pin member 50 through the first shield member, a first passage 66 extends laterally therethrough and across the receiving slot 58. The diameter of the first passage is substantially similar to that of the pin member to enable sliding receipt therein. The coupling device 50 further includes second passage 67 extending laterally through the second shield member 33 and having a diametric dimension substantially similar to that of the first passage 66. Other coupling devices may be employed as well such as the above-mentioned shrink wrap materials enveloping the shield assembly.

It will be understood that second passage 67 of the second shield member 33 will be oriented and positioned substantially in co-axial alignment with the first passage 66 when the shield assembly is in the closed position. Subsequently, the pin member 50 may be slideably inserted through the first and second passages. Thus, the pin member may also function to align and latch the two shield members together as well.

As can be appreciated from the foregoing, the invention, in its various embodiments achieves the purpose of enclosing the stent and catheter assembly in an manner substantially preventing the direct passage of radioisotopes emitted from the stent radially out of the radiation shield assembly. At the same time, the present invention addresses the problems encountered in usage of the prior art invention such as inflexible usage and maneuverability by allowing the shield assembly to be taken apart at some point during or after the stent insertion procedure.

While this invention has been described in terms of several preferred embodiments, there are alterations, permutations, and equivalents which fall within the scope of this invention. For example, the two shield members may be movably coupled by any coupling device other than a hinge, a pin member or shrink wrap material, and each shield member may be made of more than one layer. It should also be noted that there are many alternative ways of implementing the methods and apparatuses of the present invention. It is therefore intended that the following appended claims be interpreted as including all such alterations, permutations, and equivalents as fall within the true spirit and scope of the present invention.

What is claimed is:

1. A radiation shield assembly for a radioactive stent comprising:

a first shield member having a first mating surface; and a second shield member removably coupled to said first shield member, and having an opposed second mating surface cooperating with said first mating surface to substantially radially enclose the stent therebetween, said first and second mating surfaces further defining a barrier side wall therebetween extending substantially from one side of the shield assembly to an opposite side thereof such that the direct substantially linear passage of radioisotopes emitted radially from the stent and passing between the first and second mating surfaces will impact the barrier side wall, having a sufficient thickness, to substantially prevent the passage thereof radially out of said shield assembly.

2. The radiation shield assembly according to claim 1 wherein, said first mating surface and said second mating surface further cooperate to define a channel therebetween, formed and dimensioned for longitudinal receipt of the stent therein.

3. The radiation shield assembly according to claim 2 wherein, the radioactive stent is placed at a distal portion of a stent delivery catheter apparatus, and said channel extends longitudinally from one end of said shield assembly to an opposite end thereof for axial receipt of the mounted stent and the distal portion of said catheter apparatus therein.

4. The radiation shield assembly according to claim 3 further including:

a coupling device movably coupling said second shield member to the first shield member between a closed position, enclosing at least said catheter apparatus in said channel, and an open position, enabling removal of said catheter apparatus from said shield assembly.

5. The radiation shield assembly according to claim 4 wherein, said coupling device is provided by a hinge member movably mounting one edge of said first mating surface of said shield member to an opposed edge of said second mating surface of said second shield member between the closed and open positions.

6. The radiation shield assembly according to claim 4 wherein, said coupling device is provided by a shrink wrap material enveloping said shield assembly in the closed position.

7. The radiation shield assembly according to claim 3 wherein, said first mating surface of said first shield member further defines an alignment prong on one side of said channel, and said second mating surface of said second shield member further defines a recess formed and dimensioned for receipt of the alignment prong therein to align the first and second shield members when mounted together to enclose said stent in the channel.

8. The radiation shield assembly according to claim 7, wherein, said alignment prong defines the barrier side wall on one side of the channel, and extends substantially longitudinally along said channel from the one end of said shield assembly to the opposite end thereof, and said recess extends substantially longitudinally along said channel from the one end of said shield assembly to the opposite end thereof.

9. The radiation shield assembly according to claim 7, further wherein, said first mating surface of said first shield member further defines one of a second alignment prong and a second recess positioned on an opposite side of said channel, and said second mating surface of said second shield member further defines the other of a second recess and a second alignment prong, respectively, said second recess being formed and dimensioned for receipt of the second alignment prong to further align the first and second shield members when mounted together to enclose the stent in the channel.

10. The radiation shield assembly according to claim 9, wherein, said first alignment prong defines the barrier side wall on the opposite side of the channel, and extends substantially longitudinally along said channel from the one end of said shield assembly to the opposite end thereof, said first recess extends substantially longitudinally along for said channel from the one end of said shield assembly to the opposite end thereof, said second alignment prong defines the barrier side wall on one side of the channel, and extends substantially longitudinally along said channel from the one end of said shield assembly to the opposite end thereof, and said second recess extends substantially longitudinally along said channel from the one end of said shield assembly to the opposite end thereof.

11. The radiation shield assembly according to claim 3 wherein, said first mating surface of said first shield member includes
a support wall intersecting said channel,
a first alignment wall on one side of said channel disposed at an angle skewed relative said support wall, and
a second alignment wall on the opposite side of said channel disposed at an angle skewed relative said support wall, each said support wall, said first alignment wall and said second alignment wall extending from one end of the shield assembly to the opposite end thereof, and said second mating surface of said second shield member includes
an opposed support wall intersecting said channel,
a first opposed alignment wall on the one side of said channel disposed at an angle skewed relative said opposed support wall, and
a second opposed alignment wall on the opposite side of said channel disposed at an angle skewed relative said opposed support wall, each said opposed support wall, said first opposed alignment wall and said second opposed alignment wall extending from one end of the shield assembly to the opposite end thereof, wherein said first alignment wall engages said first opposed alignment wall, said second alignment wall engages said second opposed alignment wall, and said support wall engages said opposed support wall when the first and second shield members are mounted together to enclose said stent in the channel.

12. The radiation shield assembly according to claim 11, further including:
a coupling device movably coupling said second shield member to the first shield member between a closed position, enclosing at least said catheter apparatus in said channel, and an open position, enabling removal of said catheter apparatus from said shield assembly.

13. The radiation shield assembly according to claim 12, wherein,
said coupling device is provided by a pin member removably positioned in and extending through both said first shield member and said second shield member in the closed position.

14. The radiation shield assembly according to claim 2 wherein,
said first mating surface defines a first channel portion, and said second mating surface defines a second channel portion, said first channel portion and said second channel portion cooperating to collectively define said channel when the first and second shield members are mounted together to enclose said stent therein.

15. The radiation shield assembly according to claim 14, wherein,
said first mating surface of said first shield member further defines a first alignment prong on one side of said channel, and said second mating surface of said second shield member further defines a first recess formed and dimensioned for receipt of the first alignment prong therein to align the first and second channel portions when the first and second shield members are mounted together to enclose said stent in the channel.

16. The radiation shield assembly according to claim 15, wherein,
said first alignment prong defines the barrier side wall on one side of the channel, and extends substantially longitudinally along said channel from the one end of said shield assembly to the opposite end thereof, and
said first recess extends substantially longitudinally along said channel from the one end of said shield assembly to the opposite end thereof.

17. The radiation shield assembly according to claim 15, further wherein,
said first mating surface of said first shield member further defines one of a second alignment prong and a second recess positioned on an opposite side of said channel, and
said second mating surface of said second shield member further defines the other of a second recess and a second alignment prong, respectively, said second recess being formed and dimensioned for receipt of the second alignment prong therein to further align the first and second channel portions when the first and second shield members are mounted together to enclose said stent in the channel.

18. The radiation shield assembly according to claim 17, wherein,
said first alignment prong defines the barrier side wall on the opposite side of the channel, and extends substantially longitudinally along said channel from the one end of said shield assembly to the opposite end thereof,
said first recess extends substantially longitudinally along for said channel from the one end of said shield assembly to the opposite end thereof,
said second alignment prong defines the barrier side wall on one side of the channel, and extends substantially longitudinally along said channel from the one end of said shield assembly to the opposite end thereof, and
said second recess extends substantially longitudinally along said channel from the one end of said shield assembly to the opposite end thereof.

19. The radiation shield assembly according to claim 1 wherein,
the first and second shield members are composed of a polymer material.

20. The radiation shield assembly according to claim 19, wherein,
said polymer material is an acrylic.

21. The radiation shield assembly according to claim 1 wherein,
each of the first and second shield members include an inner layer and an outer layer.

22. The radiation shield assembly according to claim 21, wherein,
said inner layer is composed of a polymer material, and said outer layer is composed of a metallic material.

23. A radiation shield assembly for a radioactive stent comprising:
a first shield member and a second shield member cooperating to define a channel therebetween, formed and dimensioned for longitudinal receipt of the stent therein;

said first shield member further having a first mating surface which includes a support wall intersecting said channel, and a first alignment side wall on one side of said channel disposed at an angle skewed relative said support wall, and a second alignment side wall on the opposite side of said channel disposed at an angle skewed relative said support wall, each of the support wall and the alignment side walls extending from one end of the shield assembly to the opposite end thereof; and said second shield member further having a second mating surface which includes an opposed support wall intersecting said channel, and a first opposed alignment side wall on the one side of said channel disposed at an angle skewed relative said opposed support wall, and a second opposed alignment side wall on the opposite side of said channel disposed at an angle skewed relative said opposed support wall, each of the opposed support wall and the opposed alignment side walls extending from one end of the shield assembly to the opposite end thereof, and wherein said first alignment side wall engages said first opposed alignment side wall, said second alignment wall engages said second opposed alignment wall, and said support wall engages said opposed support wall when the first and second shield members are mounted together to enclose said stent in the channel such that the first and second mating surfaces cooperate to substantially radially enclose the stent therebetween in a manner substantially preventing the direct passage of radioisotopes emitted from the stent radially out of said shield assembly.

24. The radiation shield assembly according to claim 23 wherein, the radioactive stent is placed at a distal portion of a stent delivery catheter apparatus, and said channel extends longitudinally from one end of said shield assembly to an opposite end thereof for axial receipt of the mounted stent and the distal portion of said catheter apparatus therein.

25. The radiation shield assembly according to claim 23 further including:

a coupling device movably coupling said second shield member to the first shield member between a closed position, enclosing at least said catheter apparatus in said channel, and an open position, enabling removal of said catheter apparatus from said shield assembly.

26. The radiation shield assembly according to claim 25 wherein, said coupling device is provided by a pin member removably positioned in and extending through both said first shield member and said second shield member in the closed position.

27. A radioactive stent delivery assembly comprising:

a stent delivery catheter apparatus;

a radioactive stent placed at a distal portion of the stent delivery catheter apparatus, and a radioactive shield assembly defining a channel for longitudinal receipt of the stent and the distal portion of the stent delivery catheter therein, said shield assembly including a first shield member having a first mating surface; and a second shield member removably coupled to said first shield member, and having an opposed second mating surface cooperating with said first mating surface to substantially radially enclose the stent therebetween in a manner substantially preventing the direct substantially linear passage of radioisotopes emitted from the stent radially out of said shield assembly.

28. The radioactive stent delivery assembly according to claim 27 wherein, said channel extends longitudinally from one end of said shield assembly to an opposite end thereof for axial receipt of the mounted stent and the distal portion of said catheter apparatus therein.

29. The radioactive stent delivery assembly according to claim 28 further including, a coupling device movably coupling said second shield member to the first shield member between a closed position, enclosing at least said catheter apparatus in said channel, and an open position, enabling removal of said catheter apparatus from said shield assembly.

30. The radiation shield assembly according to claim 27 wherein, said first mating surface of said first shield member further defines a first alignment prong on one side of said channel, and extending substantially longitudinally along said channel from the one end of said shield assembly to the opposite end thereof, and said second mating surface of said second shield member further defines a first recess formed and dimensioned for receipt of the first alignment prong therein to align the first and second shield members when mounted together to enclose said stent in the channel.

31. The radiation shield assembly according to claim 30 further wherein, said first mating surface of said first shield member further defines one of a second alignment prong and a second recess positioned on an opposite side of said channel, and extending substantially longitudinally along said channel from the one end of said shield assembly to the opposite end thereof, and said second mating surface of said second shield member further defines the other of a second recess and a second alignment prong, respectively, said second recess being formed and dimensioned for receipt of the second alignment prong therein to further align the first and second shield members when mounted together to enclose said stent in the channel.

* * * * *